US00PP32155P2

(12) United States Plant Patent
Lewis

(10) Patent No.: US PP32,155 P2
(45) Date of Patent: Sep. 1, 2020

(54) ***CROCOSMIA* PLANT NAMED 'LAVA'**

(50) Latin Name: *Crocosmia X hybrida*
Varietal Denomination: Lava

(71) Applicant: Paul Lewis, Newport (GB)

(72) Inventor: Paul Lewis, Newport (GB)

( * ) Notice: Subject to any disclaimer, the term of this patent is extended or adjusted under 35 U.S.C. 154(b) by 0 days.

(21) Appl. No.: 16/602,208

(22) Filed: Aug. 28, 2019

(51) Int. Cl.
*A01H 5/02* (2018.01)

(52) U.S. Cl.
USPC ..... Plt./419

(58) Field of Classification Search
USPC ..... Plt./419
CPC ..... A01H 5/02; A01H 6/00
See application file for complete search history.

*Primary Examiner* — Keith O. Robinson
(74) *Attorney, Agent, or Firm* — C. A. Whealy

(57) ABSTRACT

A new and distinct cultivar of *Crocosmia* plant named 'Lava', characterized by its upright plant habit; strong, sturdy and resistance to lodging; moderately vigorous to vigorous growth habit; freely flowering habit; numerous and relatively large and upward-facing orange red and orange-colored flowers; and good garden performance and winter hardiness.

2 Drawing Sheets

Botanical designation: *Crocosmia* X *hybrida*.
Cultivar denomination: 'LAVA'.

BACKGROUND OF THE INVENTION

The present invention relates to a new and distinct cultivar of *Crocosmia* plant, also referred to as *Montbretia*, botanically known as *Crocosmia* X *hybrida* and hereinafter referred to by the name 'Lava'.

The new *Crocosmia* plant is a product of a planned breeding program conducted by the Inventor in Carisbrook, Newport, The Isle of Wight, United Kingdom. The objective of the breeding program is to create new upright and strong *Crocosmia* plants with large attractive upward-facing flowers, a long flowering period and winter hardiness.

The new *Crocosmia* plant originated from a cross-pollination made by the Inventor in Carisbrook, Newport, The Isle of Wight, United Kingdom on Jul. 10, 2007 of two unnamed seedling selections of *Crocosmia* X *hybrida*, not patented. The new *Crocosmia* plant was discovered and selected by the Inventor as a single flowering plant from within the progeny of the stated cross-pollination in a controlled greenhouse environment in Carisbrook, Newport, The Isle of Wight, United Kingdom on Aug. 14, 2009.

Asexual reproduction of the new *Crocosmia* plant by divisions in a controlled greenhouse environment in Carisbrook, Newport, The Isle of Wight, United Kingdom since the spring of 2010 has shown that the unique features of this new *Crocosmia* plant are stable and reproduced true to type in successive generations.

SUMMARY OF THE INVENTION

Plants of the new *Crocosmia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Lava'. These characteristics in combination distinguish 'Lava' as a new and distinct *Crocosmia* plant:

1. Upright plant habit; strong, sturdy and resistance to lodging.
2. Moderately vigorous to vigorous growth habit.
3. Freely flowering habit.
4. Numerous and relatively large and upward-facing orange red and orange-colored flowers.
5. Good garden performance and winter hardiness.

Plants of the new *Crocosmia* differ primarily from plants of the parent selections in the following characteristics:

1. Plants of the new *Crocosmia* are more freely flowering than plants of the parent selections.
2. Plants of the new *Crocosmia* have larger flowers than plants of the parent selections.
3. Plants of the new *Crocosmia* are more winter hardy than plants of the parent selections.

Plants of the new *Crocosmia* can be compared to plants of *Crocosmia masonianum* 'Okovango', not patented. In side-by-side comparisons, plants of the new *Crocosmia* differ primarily from plants of 'Okovango' in flower color as plants of the new *Crocosmia* have orange red and orange-colored flowers whereas plants of 'Okovango' have soft apricot orange-colored flowers. In addition, plants of the new *Crocosmia* have larger flowers than plants of 'Okovango'.

BRIEF DESCRIPTION OF THE PHOTOGRAPHS

The accompanying colored photographs illustrate the overall appearance of the new *Crocosmia* plant showing the colors as true as it is reasonably possible to obtain in colored reproductions of this type. Colors in the photographs may differ slightly from the color values cited in the detailed botanical description which accurately describe the colors of the new *Crocosmia* plant.

The photograph on the first sheet comprises a side perspective view of typical flowering plants of 'Lava' grown in an outdoor nursery.

The photograph on the second sheet is a close-up view of typical inflorescences of 'Lava'.

DETAILED BOTANICAL DESCRIPTION

The aforementioned photographs and following observations and measurements describe plants of the new *Crocosmia* grown during the summer in an outdoor nursery in Hillegom, The Netherlands. During the production of the plants, day temperatures ranged from 16° C. to 30° C. and night temperatures ranged from 8° C. to 20° C. Plants were one year old when the photographs and the description were taken. In the following description, color references are made to The Royal Horticultural Society Colour Chart, 2015 Edition, except where general terms of ordinary dictionary significance are used.

Botanical classification: *Crocosmia* X *hybrida* 'Lava'.

Parentage:

*Female, or seed, parent*.—Unnamed seedling selection of *Crocosmia* X *hybrida*, not patented.

*Male or pollen parent*.—Unnamed seedling selection of *Crocosmia* X *hybrida*, not patented.

Propagation:

*Type*.—By in vitro meristem culture.

*Time to initiate roots*.—About one week at temperatures about 20° C.

*Time to produce a rooted young plant*.—About seven weeks at temperatures ranging from 15° to 20° C.

*Root description*.—Medium in thickness, fleshy and fibrous; brown in color, actual color of the roots is dependent on substrate composition, water quality, fertilizer type and formulation, substrate temperature and physiological age of roots.

*Rooting habit*.—Low branching; medium density.

*Corms*.—To date, corm development has not been observed on plants of the new *Crocosmia*.

Overall plant description:

*Plant and growth habit*.—Upright plant habit; overall plant shape, narrowly oblong with slightly arching flowering stems; moderately vigorous to vigorous growth habit; strong stems that develop at the plant base and resist lodging; moderate to rapid growth rate.

*Plant height, soil level to top of foliar plane*.—About 75 cm.

*Plant height, soil level to top of floral plane*.—About 107 cm.

*Plant diameter* (*spread*).—About 22.5 cm.

Stem description:

*Aspect*.—Mostly upright.

*Length*.—About 66 cm.

*Diameter*.—About 8 mm.

*Internode length*.—About 18.5 cm.

*Strength*.—Strong.

*Texture and luster*.—Smooth, glabrous, waxy; slightly glossy.

*Color, when developing*.—Close to 199A.

*Color, developed*.—Close to 199A to 199B; under surface tinged with close to 146C; waxy cuticle, close to 198B to 198C.

Leaf description:

*Appearance*.—Simple, distichous; sessile.

*Quantity per stem*.—About eight.

*Length*.—About 56.8 cm.

*Width*.—About 3.8 cm.

*Shape*.—Ensiform, strongly plicate.

*Apex*.—Narrowly acuminate.

*Base*.—Sheathing; sheath is about 34.4 cm in length, 1 cm in width and close to 146B in color.

*Margin*.—Entire.

*Texture and luster, upper and lower surfaces*.—Smooth, glabrous; matte.

*Venation pattern*.—Camptodrome.

*Color*.—Developing leaves, upper and lower surfaces: Close to between 146A and 147B. Fully expanded leaves, upper and lower surfaces: Close to between 146A and 147B; venation, close to 146A.

Flower description:

*Flower type and habit*.—Single tubular flowers arranged on terminal rhipidiums; flowers sessile; flowers face mostly outwardly and upward-facing; perianth segments fused; freely flowering habit with about 89 flowers developing per inflorescence.

*Natural flowering season*.—Flowering continuous in July and August in The Netherlands; plants begin flowering about six months after planting.

*Fragrance*.—None detected.

*Flower longevity on the plant*.—About ten days; flowers not persistent.

*Flower buds*.—Length: About 2.3 cm. Diameter: About 5 mm. Shape: Narrowly obovate, slightly curved downward. Texture and luster: Smooth, glabrous, moderately velvety; matte. Color: Close to 46A and 46B; towards the base, close to 152C and 152D; immature sepals, upper surface, close to 183A and 183B; immature sepals, lower surface, close to 144B.

*Inflorescence length*.—About 35.6 cm.

*Inflorescence diameter*.—About 28 cm.

*Flower diameter*.—About 4.6 cm by 5.5 cm.

*Flower length*.—About 6.3 cm.

*Flower throat diameter*.—About 1.2 cm.

*Flower tube length*.—About 3 cm.

*Flower tube diameter*.—About 8 mm to 9 mm.

*Perianth*.—Arrangement: Six arranged in two whorls, each whorl with three segments fused towards the base; inner whorl of perianth segments has a larger dorsal segment and two smaller lateral segments that are similar to outer whorl segments. Inner perianth dorsal segment: Length: About 6.2 cm. Width: About 2.3 cm. Shape: Obovate; proximally, 52.5% of the length of the segment is fused into a tube. Apex: Obtuse. Margin: Entire. Texture and luster, upper and lower surfaces: Smooth, glabrous, moderately velvety; matte. Color, when opening, upper surface: Close to 33A. Color, when opening, lower surface: Close to 33A, 33B and 42B. Color, fully opening, upper surface: Close to N30B; towards the throat, close to 28A; venation, similar to lamina; color does not change with development. Color, fully opening, lower surface: Close to N30A to N30B; venation, close to 42A; color does not change with development. Inner perianth lateral segments and outer perianth segments: Length: About 4.8 cm. Width, inner lateral segments: About 1.6 cm. Width, outer segments: About 1.3 cm. Shape: Obovate; proximally, 52.5% of the length of the segment is fused into a tube. Apex: Obtuse. Margin: Entire. Texture and luster, upper and lower surfaces: Smooth, glabrous, moderately velvety; matte. Color, when opening, upper surface: Close to 33A. Color, when opening, lower surface: Close to 33A, 33B and 42B. Color, fully opening, upper surface: Close to N30A to N30B; venation, similar to lamina; color does not change with development. Color, fully opening, lower surface: Close to 34A; towards the base, close to N25A and N25B; venation, close to 42A; color does not change with development. Flower throat and tube: Texture and luster: Smooth, glabrous, moderately velvety; matte. Color, throat: Close to N34A and 46A flushed with close to 14A; venation, similar to lamina. Color, tube: Close to 33B; proximally, close to 23A; venation, similar to lamina.

*Sepals*.—Arrangement: Three in a single whorl. Length: About 1 cm. Width: About 5 mm. Shape: Broadly oblong. Apex: Praemorse. Base: Broadly cuneate, fused. Margin: Entire. Texture and luster, upper surface: Smooth, glabrous; slightly glossy. Texture and luster, lower surface: Smooth, glabrous; matte. Color, when opening and fully opened, upper surface: Close to 179B; towards the base, close to 146B. Color, when opening and fully opened, lower surface: Close to 183A tinged with close to 146B.

*Peduncles*.—Length: About 34.7 cm. Diameter: About 5 mm. Strength: Strong. Angle, primary peduncles: Proximally, erect; distally, arching to about 30° from vertical. Angle, lateral peduncles: About 40° from primary peduncle axis. Texture: Smooth, glabrous, waxy; matte. Color, upper surface: Close to 200B and N200A; waxy cuticle, close to 198B to 198C. Color, lower surface: Close to 146B; waxy cuticle, close to 198B to 198C.

*Reproductive organs*.—Stamens: Quantity per flower: Typically three. Filament length: About 3 cm. Filament color: Distally, close to 25B; proximally, close to 12A. Anther shape: Narrowly sagittate. Anther size: About 9 mm by 1.25 mm. Anther color: Close to 21C. Pollen amount: Scarce. Pollen color: Close to 12A. Pistils: Quantity per flower: One. Pistil length: About 5.6 cm. Style length: About 5 cm. Style color: Distally, close to N25A to N25B; proximally, close to 12A. Stigma shape: Three-parted, curved. Stigma size: About 6 mm by 6 mm. Stigma color: Close to 20A. Ovary color: Close to 143C.

*Fruits and seeds*.—To date, fruit and seed development have not been observed on plants of the new *Crocosmia*.

Pathogen & pest resistance: To date, plants of the new *Crocosmia* have not been observed to be resistant to pathogens and pests common to *Crocosmia* plants.

Garden performance: Plants of the new *Crocosmia* have been observed to have good garden performance, to resist lodging and to tolerate wind, rain and temperatures ranging from about −12° C. to about 35° C.; plants of the new *Crocosmia* are suitable for USDA Hardiness Zones 6 to 10.

It is claimed:

1. A new and distinct *Crocosmia* plant named 'Lava' as illustrated and described.

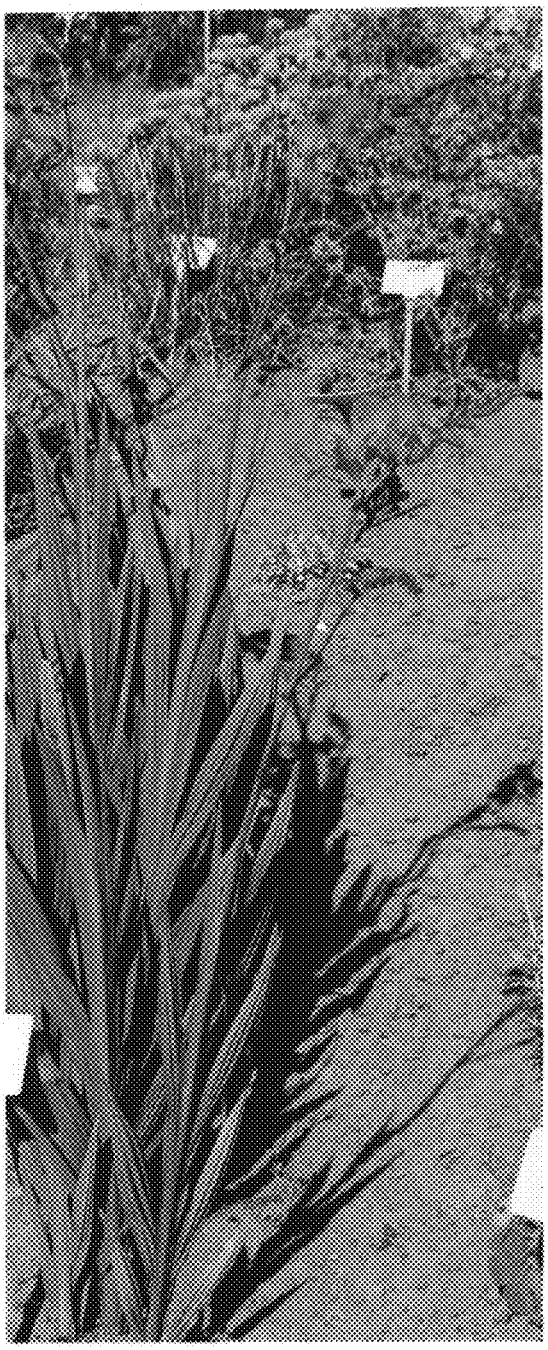

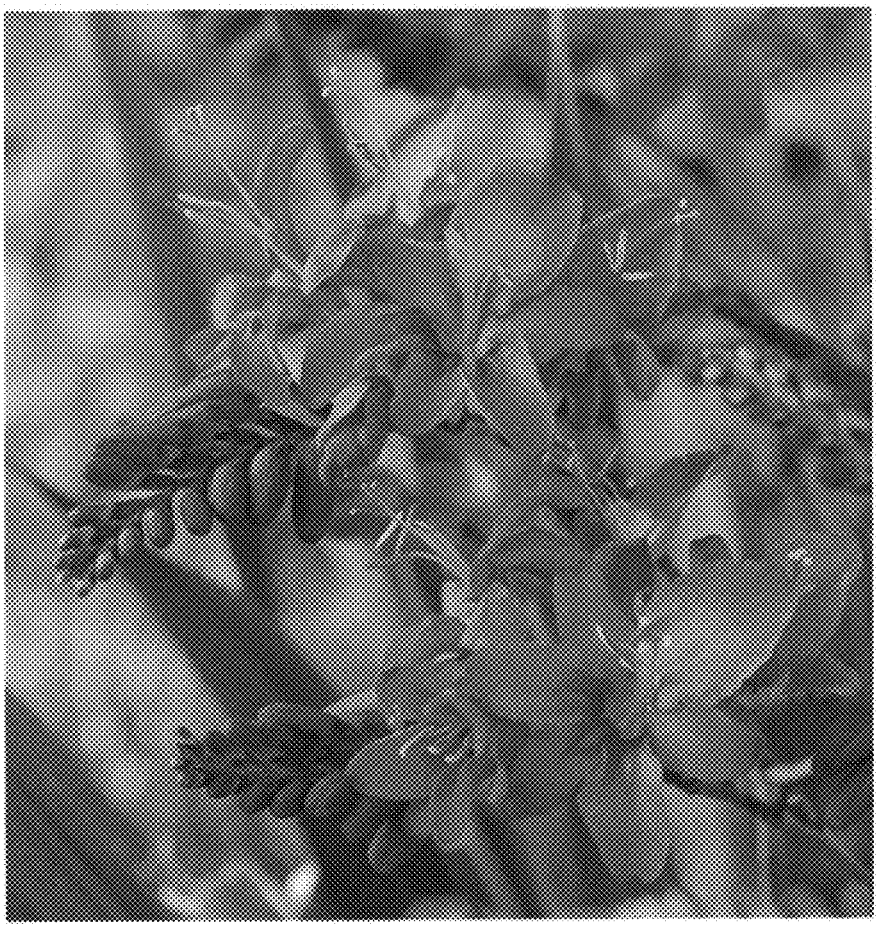

* * * * *